United States Patent [19]

de Tavares

[11] Patent Number: 4,709,438
[45] Date of Patent: Dec. 1, 1987

[54] TOOTHBRUSH WITH GRAVITY SWITCH

[76] Inventor: Joaquim de Tavares, No. 35, Lehmweg, 2000 Hamburg 20, Fed. Rep. of Germany

[21] Appl. No.: 846,452

[22] Filed: Mar. 31, 1986

[51] Int. Cl.⁴ .............................................. A46B 13/02
[52] U.S. Cl. ................................. 15/167 A; 15/167 R
[58] Field of Search ......................... 15/167 R, 167 A; 200/221; 132/84 R

[56] References Cited

U.S. PATENT DOCUMENTS

| Re. 21,673 | 12/1940 | Murad | 200/221 |
| 1,638,133 | 8/1927 | Walker | 200/211 |
| 2,186,818 | 1/1940 | Brown | 200/221 |

FOREIGN PATENT DOCUMENTS

| 3332247 | 3/1985 | Fed. Rep. of Germany | 15/167 R |
| 3334841 | 4/1985 | Fed. Rep. of Germany | 15/167 R |

Primary Examiner—Robert P. Swiatek
Assistant Examiner—Adriene J. Lepiane
Attorney, Agent, or Firm—John C. Smith, Jr.

[57] ABSTRACT

A toothbrush is provided which has a headpiece with a cylindrical brush and a handle. By means of a gravity switch the direction of rotation of the brush is reversed according to the turning movement of the handle, in order to automatically maintain a direction of rotation of the brush from the gums to the crown of the tooth. In order to obtain the correct position of the toothbrush, the brush is provided with a protecting cap leaving an opening in order to form a working region. The gravity switch is arranged parallel to the plane of the free working region of the brush.

6 Claims, 9 Drawing Figures

FIG. 6
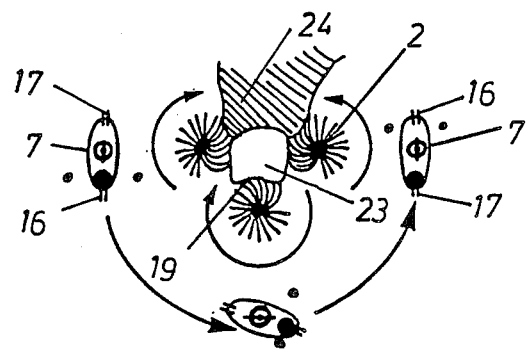
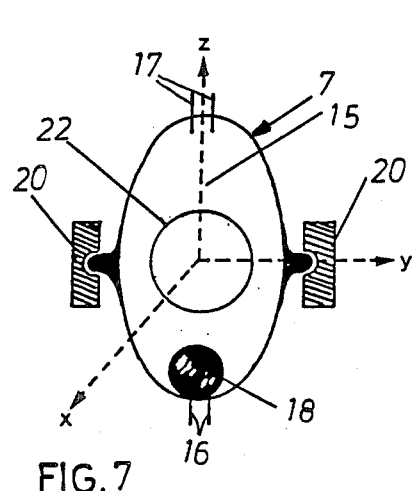
FIG. 7
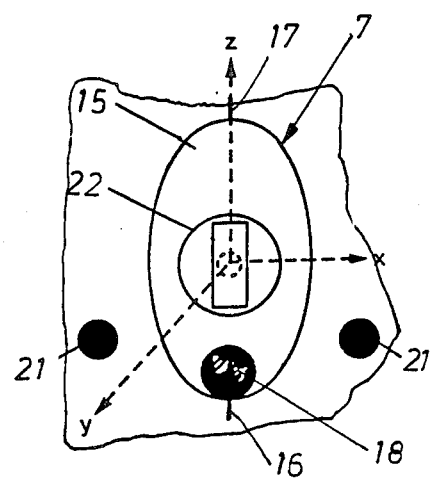
FIG. 8
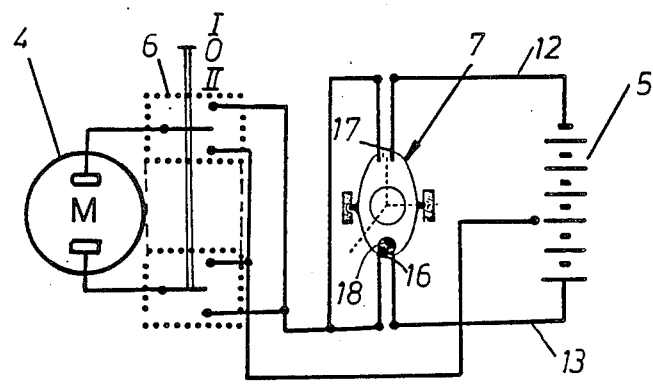
FIG. 9

TOOTHBRUSH WITH GRAVITY SWITCH

BACKGROUND OF THE INVENTION

This invention relates to a toothbrush provided with a headpiece carrying a brush and with a handle accommodating an electric motor with a battery and switching elements, the brush being formed cylindrically and performing a rotational movement via a driving shaft for the purpose of dental care.

Constructions of this kind as well as toothbrushes having a vibrating brush are known. These known devices have the deficiency that the brush possibly has a direction of rotation towards the gums and thus causes injuries of the gums and small food particles are pushed under the gums. Furthermore, by a vibrating brush the gums are pushed back and forth, so that a destruction of the tissue and later bleeding from the gums occur.

SUMMARY OF THE INVENTION

It is the object of the present invention to avoid the above-mentioned deficiencies and to provide a toothbrush in which the change in the direction of rotation of the brush is effected automatically in order to ensure a movement of the bristles of the brush from the gums towards the crown of the tooth.

To attain this object, the invention provides a toothbrush provided with a headpiece carrying a brush and with a handle accommodating an electric motor with a battery and switching elements, the brush being formed cylindrically and performing a rotational movement about a rotational axis via a driving shaft for the purpose of dental care, wherein the cylindrical brush is provided with a protecting cap which at a distance from the rotational axis of the brush leaves free an opening forming a free working region, and the electric motor and thus the direction of rotation of the brush are reversible by means of a gravity switch arranged parallel to the plane of the free working region in such a manner that the direction of rotation from the gums to the crown of a tooth is automatically reversed when turning the handle.

Thereby, it is possible to adjust the direction of rotation automatically when the toothbrush is turned during the care of the inner and outer region of the teeth so that the teeth are brushed always from the gums to the crowns.

In order to achieve a simple basic adjustment for the region of the teeth, it is proposed to additionally provide the handle with a switch for switching on and reversing the electric motor for starting and changing the direction of rotation in order to adjust a basic position during dental care of the upper and lower jaw.

A simple construction for realizing a gravity switch for this purpose is achieved in that the gravity switch is formed by a hollow capsule having in its interior a mercury ball as contact means, said capsule having at its two poles in each case two contacts to be connected, the large axis of the capsule being arranged transversely to the rotational direction in the plane of the working region of the brush.

In order to maintain a contact stability in the gravity switch for the case of a deviation from the horizontal when holding the whole construction, it is proposed that the capsule for forming the gravity switch is arranged so as to be pivotable transversely to the plane of the working region of the brush by means of bearing elements, the pivoting movement of the capsule being limited by laterally associated stops in order to maintain the connection between the contacts.

For the purpose of achieving in a simple manner a switching delay when reversing the direction of rotation it is proposed that the capsule comprises a ball arranged approximately in its center, a distance of about one third of the diameter of the mercury ball being left between the walls of the capsule and the ball.

An advantageous construction of the capsule for the gravity switch is achieved in that the capsule is elliptically formed. Thereby, it is possible to achieve stable contact conditions at the pole ends of the capsule by means of a mercury ball.

BRIEF DESCRIPTION OF THE DRAWINGS

An embodiment of the invention will now be described by way of example and with reference to the accompanying drawings in which:

FIG. 6 is a principle representation of the direction of rotation of the bristles at a tooth and an associated position of the gravity switch;

FIG. 7 is a representation of the gravity switch;

FIG. 8 is a representation according to FIG. 7 turned by 90°, and

FIG. 9 is a switch diagram of the arrangement.

DESCRIPTION OF THE PREFERRED EMBODIMENT

Figure 1:
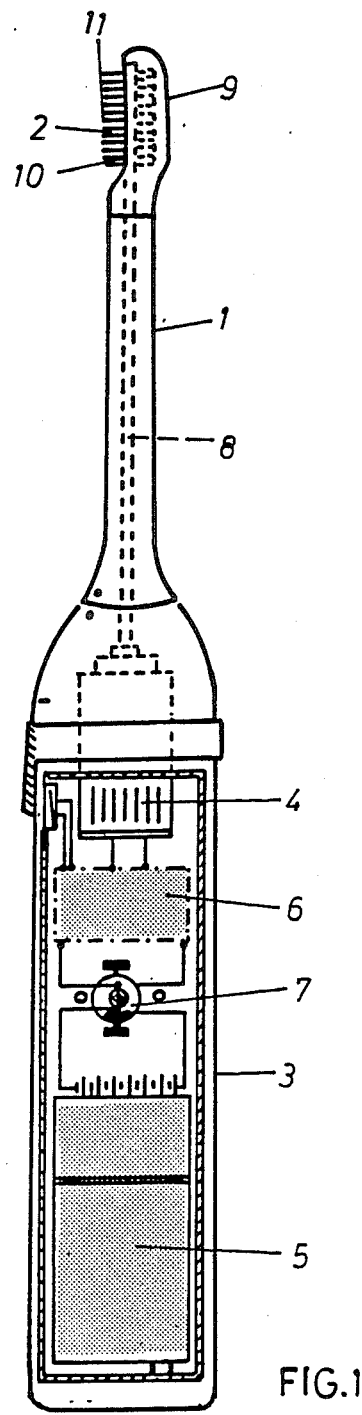
FIG. 1 is a side elevational view of a toothbrush according to the present invention with a cut up handle.
Figure 2:
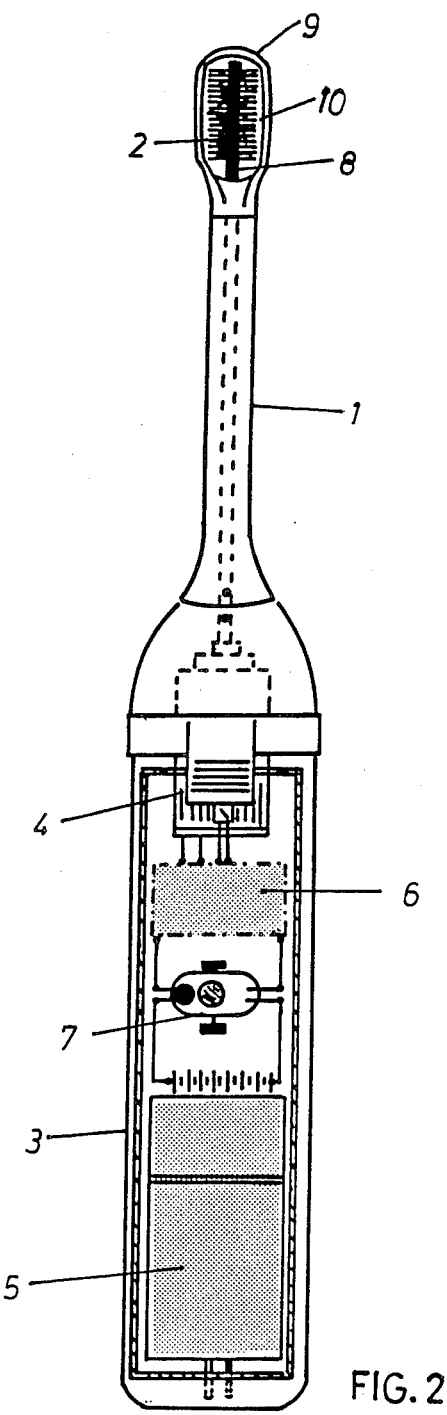
FIG. 2 is a side elevational view according to FIG. 1 turned by 90°.
Figure 3:
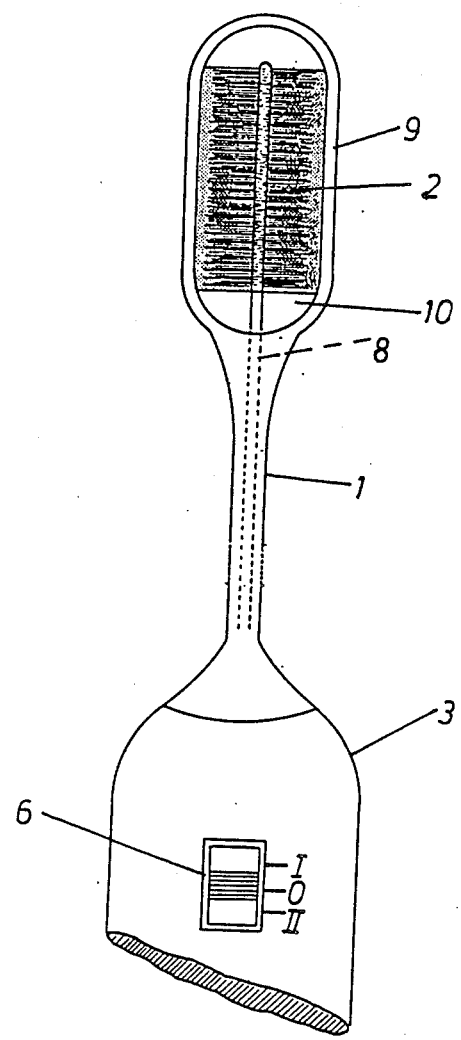
FIG. 3 is a view of the top region of the toothbrush with a switch for switching on different directions of rotation.
Figure 4:
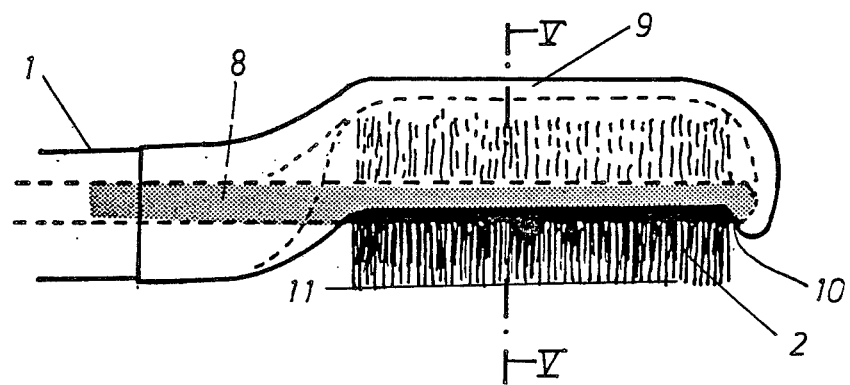
FIG. 4 is a side elevational view, on an enlarged scale, of the cylindrical brush in the headpiece.
Figure 5:
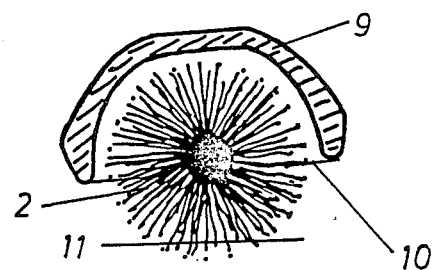
FIG. 5 is a section, on the line V—V of FIG. 4.

FIGS. 1 and 2 show a toothbrush with a headpiece 1 which carries at its upper end a cylindrical brush 2, and with a handle 3 at its other end accommodating an electric motor 4 with a battery 5, a switch 6 and a gravity switch 7. The electric motor 4 drives the brush 2 via a shaft 8 which passes through the headpiece 1 and forms the rotational axis. The brush 2 is provided with a protecting cap 9 which has an opening 10 and leaves free a working region 11.

The control of the electric motor 4 is effected by means of the switch 6 which in position I sets a clockwise rotation of the brush 2 and in position II a counterclockwise rotation of the brush 2. Two connecting lines 12 and 13 (see FIG. 9) coming from the battery 5 run across the gravity switch 7 which is formed by an elliptical hollow capsule 15. Each of the two pole ends of the capsule 15 has two contacts 16 and 17 which are bridged by a mercury ball 18. The large axis z (see FIGS. 7 and 8) of the capsule 15 is arranged transversely to the rotational axis in the plane formed by the working region 11 of the brush 2 and bridges by means of the mercury ball 18 for example the contacts 16.

FIG. 6 shows how a tooth 23 is arranged in the gums 24 and how the brush 2 rotates from the gums to the crown 19 of the tooth. At the other side of the tooth 23, the mercury ball 18 is located on the other side of the capsule 15 so that the rotational direction of the brush 2 is reversed by the switching operation. By the turning movements of the handle 3 which are necessary to keep the contact between the working region 11 and the tooth 23, also the gravity switch 7 together with its capsule 15 is rotated.

In this case, the capsule 15 of the gravity switch 7 is arranged by bearing elements 20 so as to be pivotable about its Y axis, the pivotal movement being limited by laterally associated stops 21. By this means, the contact is maintained by the mercury ball 18 also when deviating from the horizontal position.

Furthermore, a ball 22 is arranged approximately in the center of the capsule 15, a distance of about one third of the diameter of the mercury ball 18 being left between the walls of the capsule 15 and the ball 22. By the increased friction resulting thereby in this region, a desired delay occurs when the gravity switch 7 is switched over and thus also the change in the direction of rotation of the brush 2 is effected with delay.

The invention may be embodied in other specific forms without departing from the spirit or essential characteristics thereof. The embodiment is therefore to be considered in all respects as illustrative and not restrictive.

What is claimed is:

1. A toothbrush provided with a headpiece carrying a brush and with a handle accommodating an electric motor with a battery and switching elements, the brush being formed cylindrically and performing a rotational movement about a rotational axis via a driving shaft extending between said brush and said electric motor for the purpose of dental care, wherein the cylindrical brush is provided with a protecting cap which is stationary with respect to said handle and, at a distance from the rotational axis of the brush, has an opening forming a free working region, the electric motor and thus the direction of rotation of the brush being reversible, a gravity switch, and first and second electrical circuit means connecting said motor to said switch, said gravity switch being arranged to close said first electrical circuit means and open said second electrical circuit means to drive said motor in one direction when said handle is in one position and to open said first electrical circuit means and close said second electrical circuit means to drive said motor in the opposite direction when said handle is turned about said axis from said one position to a further position such that the surface of said brush is automatically caused to move in a direction from the gums to the crown of each tooth by controlling the position of said handle.

2. A toothbrush as claimed in claim 1, wherein the handle is additionally provided with a switch for switching on and reversing the electric motor for starting and changing the direction of rotation to adjust a normal basic position during dental care.

3. A toothbrush as claimed in claim 1, wherein said gravity switch comprises a hollow capsule having in its interior a mercury ball as circuit closing and opening means, said capsule having at each of two spaced locations a pair of contacts, one of said pair of contacts being connected to said first electrical circuit means and the other pair of contacts being connected to said second electrical circuit means, the spaced locations of said pairs of contacts defining a straight line transverse to said rotational axis.

4. A toothbrush as claimed in claim 3, further comprising means mounting said capsule for pivotal movement about an axis transverse to a plane defined by said working region of said brush and stop means for limiting the pivotal movement of the capsule in order to maintain connection between each of said pair of contacts during limited turning of said handle.

5. A toothbrush as claimed in claim 3, further comprising a ball arranged approximately in the center of said capsule, a distance of about one third of the diameter of said mercury ball being maintained between the walls of the capsule and the ball.

6. A toothbrush as claimed in claim 3, wherein said capsule is elliptically formed.

* * * * *